United States Patent [19]

Guibert

[11] 4,384,191
[45] May 17, 1983

[54] GALLEY MEAL PROCESSING SYSTEM

[75] Inventor: Raul Guibert, Los Angeles, Calif.

[73] Assignee: Sunset Ltd., Los Angeles, Calif.

[21] Appl. No.: 322,085

[22] Filed: Nov. 17, 1981

Related U.S. Application Data

[63] Continuation of Ser. No. 97,787, Nov. 27, 1979, Pat. No. 4,307,286.

[51] Int. Cl.³ .............................................. H05B 1/00
[52] U.S. Cl. ...................................... 219/400; 99/447; 99/480; 126/21 A; 126/110 A; 219/271; 219/385
[58] Field of Search ............... 219/386, 385, 388, 400, 219/401, 367, 369, 370, 371, 372; 126/21 A, 110 A, 261, 268, 248, 285 B, 285 A; 99/480, 355, 447; 312/236

[56] References Cited

U.S. PATENT DOCUMENTS

| | | | |
|---|---|---|---|
| 3,439,665 | 4/1969 | Stromquist | 126/21 A |
| 4,010,341 | 3/1977 | Tshammar | 219/400 |
| 4,089,322 | 5/1978 | Guilbert | 126/261 |
| 4,113,977 | 9/1978 | Hochstrasser | 219/400 X |
| 4,307,286 | 12/1981 | Guilbert | 219/400 |

FOREIGN PATENT DOCUMENTS 122267  7/1948  Sweden ............................ 219/400

Primary Examiner—Volodymyr Y. Mayewsky
Attorney, Agent, or Firm—Michael Ebert

[57] ABSTRACT

A system for installation on aircraft to serve trays containing precooked food to passengers, the food-loaded trays being placed in the aircraft in the cold state and being heated to a service temperature level. The system includes a locker adapted to accommodate a bank of open-end racks, each having a stack of trays therein separated by air spaces, the front ends of the racks facing the door of the locker. Behind the racks is a hot air modulator in the form of a shallow box having a broad, continuously driven tape therein, the front course of the advancing tape facing the rear ends of the racks through windows in the box which register with these ends. The tape has endless trains of holes punched therein, each train lying in a plane intersecting a respective air space between trays in the stacks. Air drawn from the free region between the front door of the locker and the front ends of the racks is caused by a blower to pass through a heater station. The blower forces the air into the box from which the air is projected through the trains of holes into the air spaces to transfer heat in the food-loaded trays.

12 Claims, 6 Drawing Figures

GALLEY MEAL PROCESSING SYSTEM

RELATED APPLICATIONS

This application is a continuation-in-part of my earlier application Ser. No. 097,787, filed Nov. 27, 1979, (now U.S. Pat. No. 4,307,286) which in turn relates back to a series of earlier-filed applications identified therein. The entire disclosures of these related cases are incorporated herein by reference.

BACKGROUND OF INVENTION

This invention relates generally to convenience food service techniques in which a meal is first cooked, then refrigerated and stored, and subsequently reheated; and more particularly to a system for use on aircraft for reheating pre-cooked meals without degrading the basic texture, flavor and nutritional qualities of the meal.

In long distance commercial airline flights, it is customary to provide passengers with a hot meal. To this end, the present practice is to cook the meals in a commissary, the meals being placed in sealed trays and then refrigerated. These trays are thereafter transported to airports where they are loaded before flight into partitioned lockers on planes. Electrical heating elements are incorporated in the partitions so that the lockers serve as ovens for reheating the refrigerated meals to a temperature suitable for serving.

Though airlines generally employed experienced and skilled chefs to supervise the en masse preparation of meals in commissaries and care is exercised in choosing basic ingredients of good quality, it is nevertheless a fact that most meals served by airlines are at best of mediocre quality. Thus the typical meat dish leaves much to be desired in terms of appearance, taste and flavor. Certainly a steak served on a plane is a far cry from a steak served in a first-class restaurant, even though in both cases, use is made of meat of prime quality. This is also true of vegetables, which when originally cooked are of good, acceptable quality, yet when served in an airline tray are often overcooked and unappetizing.

In reheating a pre-cooked meal, it is difficult, when going from the refrigerated state to an adequately heated service condition, to avoid a situation in which the core of the product is still cold even though the outer layer is quite hot. And when one seeks to ensure that the body of the food is hot throughout, there is a tendency to overheat the meal and thereby re-cook it with a resultant loss of nutritional value and flavor.

An electrically-operated food locker in an aircraft functions essentially as a conventional reheating oven and suffers from serious heat transfer and control problems. In such ovens, one necessarily goes through a heat-up phase during which the temperature of the pre-cooked meal must be raised from its initial cold state to a service temperature level, at which point the food-loaded trays must be maintained at a service temperature level until such time as the trays are removed from the locker and brought by attendants to the seats of passengers.

During the heat-up phase, the rate of heat transfer from the heated air in the locker to the relatively cold food-loaded trays depends on the temperature differential; the greater the difference between the air temperature and the food temperature, the more rapid the rate of heat transfer. Since the hot air temperature throughout the locker is at a fairly uniform level, the transfer rate at the outset of heating in the heat-up phase is very rapid; but as the difference in temperature between the hot air and the food thereafter diminishes, the rate of transfer becomes increasingly slow and quite sluggish as the service temperature is approached.

Assuming that the food in the trays is initially at a temperature of about 10° F. and that it is necessary to raise the food temperature to a service level of about 150° F., and further assuming a hot air temperature of about 165° F. in the locker to avoid re-cooking, then at the outset of the heat-up phase, there will be a sharp differential giving rise to very rapid heating. But as this temperature differential diminishes in the course of the heat-up phase, the rate of heat transfer slows down. When, for example, the food temperature reaches 130° F., then the temperature differential relative to the heated air is only 35° F., and it takes a relatively long time before the food temperature can be raised to the service temperature of 150° F., at which point the heat-up phase is conducted and a service phase is initiated.

Thus if one plots a curve of food temperature (10° F. to 150° F.) vs. time in the heat-up phase, the resultant curve for a hot-air temperature of 165° F. will exhibit a sharp rise from 10° F. to about 100° F. within a fairly short time interval, the curve thereafter leveling off as the temperature goes more gradually from 100° F. to 150° F. As a result, the duration of the heat-up phase is unduly prolonged, which in some situations may be a practical disadvantage. If, for instance, the aircraft lockers are loaded with cold food trays which must be made available for service to passengers in about one half-hour after loading, this time may be inadequate to bring the meals to the proper service level.

On the other hand, while on a given flight the waiting period before meals are to be served may be adequate for the heat-up phase, because of unpredictable flight delays it may be several hours before the meals are actually served to passengers. Thus the phase during which food must be maintained in the lockers at a service temperature, instead of being, say, a half-hour period, may run for three or four hours or even longer.

As a practical matter, with electrically-operated ovens, it is difficult to maintain food at a substantially constant service temperature level for a prolonged period. Consequently, should there by an unexpected flight delay, the meals in the lockers may be recooked, dried out, and rendered unpalatable.

In my above-identified copending application of which the present application is a continuation-in-part, there is provided a system adapted to rapidly raise the temperature of a pre-cooked meal from a cold or frozen state in a manner bringing the internal temperature of the entire body of the meal to substantially the same predetermined elevated service temperature level, the meal thereafter being maintained indefinitely at the service temperature level without recooking.

In the system disclosed in my copending application, during the heat-up phase the cold pre-cooked meals are raised in temperature by periodic pulses of hot air which flow past the trays at high velocity, the temperature of the pulses being well above the predetermined elevated service temperature level, whereby the temperature differential between the heated air and the food is high even when the food approaches the service temperature level, thereby effecting a high rate of heat transfer and causing the food to reach the service temperature level quickly without, however, excessive heating thereof.

To this end, there is provided a thermally-insulated chamber having a receiving station for the trays flanked by input and output plenums. A main flow loop is provided in which the chamber is connected in a continuous flow path in series with heater station and an air pump or blower in an arrangement in which air drawn via an output line from the output plenum and creating a negative pressure therein is conducted through the heater station and then forced in the heated state through an input line leading into the input plenum to create a positive pressure therein. The resultant pressure differential between the plenums causes heated air to flow at high velocity through the section to heat the meals contained therein.

A by-pass extending between the input to the heater station and the junction of the chamber and the pump in the pump flow line defines a feedback flow loop which excludes the chamber. A damper mechanism at this junction is cyclically driven to periodically block the flow of heated air through the main loop into the chamber and to divert the flow into the feedback loop for recirculation therein.

As a consequence, main loop flow through the chamber assumes the form of a pulsatory wave whose fluidic pulses have a peak temperature whose level is well above the pre-determined temperature level and whose relaxation periods are at a temperature below this predetermined level, thereby promoting rapid heat transfer in the body of the food without, however, raising the surface temperature thereof above this level. This action is continued until the entire body of the product is at the desired service temperature level, at which point the system is operated in a service phase to maintain this level indefinitely without overheating the food product.

The pulsating hot-air system disclosed in my copending patent application will function in any environment including an airplane. However, the typical plane has very limited space available for accommodating food storage and heating facilities. It is necessary, therefore, to design a pulsating hot-air system which will operate effectively within these constraints.

SUMMARY OF INVENTION

In view of the foregoing, the main object of this invention is to provide a system especially adapted to operate on aircraft, and which during a heat-up phase acts to rapidly raise the temperature of pre-cooked cold meals contained in trays to a service temperature level and to thereafter act in a service phase to maintain the meals at the service temperature level indefinitely without impairing the quality of the heated meals.

More particularly, an object of the invention is to provide a system of the above type to effect heating by means of a pulsatory wave of hot air, which wave is composed of periodic hot air pulses separated by relaxation intervals.

Also an object of the invention is to provide a system of the above type which is highly compact and which is adapted to fit into the available food handling space in a typical aircraft.

Briefly stated, a system for use on aircraft to serve trays containing pre-cooked food to passengers, the food-loaded trays being placed in the aircraft in the cold state and being heated to a service temperature level. The system includes a thermally insulated locker adapted to accommodate a bank of open-ended racks, each having a stack of trays therein separated by air spaces, the front ends of the racks facing the door of the locker. Behind the racks is a hot air modulator in the form of a shallow box having a broad continuous tape therein, the front course of the advancing tape facing the rear end of the racks through open windows in the box which register with these ends.

The tape is provided with endless trains of holes each train lying in a plane intersecting a respective air space between the trays in the stacks. Air drawn from the free region between the front door of the locker and the front ends of the racks is caused by a blower to pass through a heater station, the blower forcing the heated air into the box from which the air is projected at high velocity through the trains of holes into the air spaces to transfer heat to the food in the trays.

Each endless train is composed of alternating large and small hole sections whereby when a large hole section is aligned with a given rack, a large volume of hot air is blown therein, and when a small hole section is so aligned, a much smaller volume of hot air is projected, thereby subjecting the trays in the racks to a pulsatory hot air wave.

OUTLINE OF DRAWINGS

For a better understanding of the invention as well as other objects and further features thereof, reference is made to the following detailed description to be read in conjunction with the accompanying drawings, wherein:

FIG. 1 shows, in perspective, the racks and the hot-air modulator included in a system in accordance with the invention;

FIG. 2 schematically illustrates the essential components of the system;

FIG. 3 separately illustrates the tape included in the modulator;

DESCRIPTION OF INVENTION

The Basic System

Figure 1:
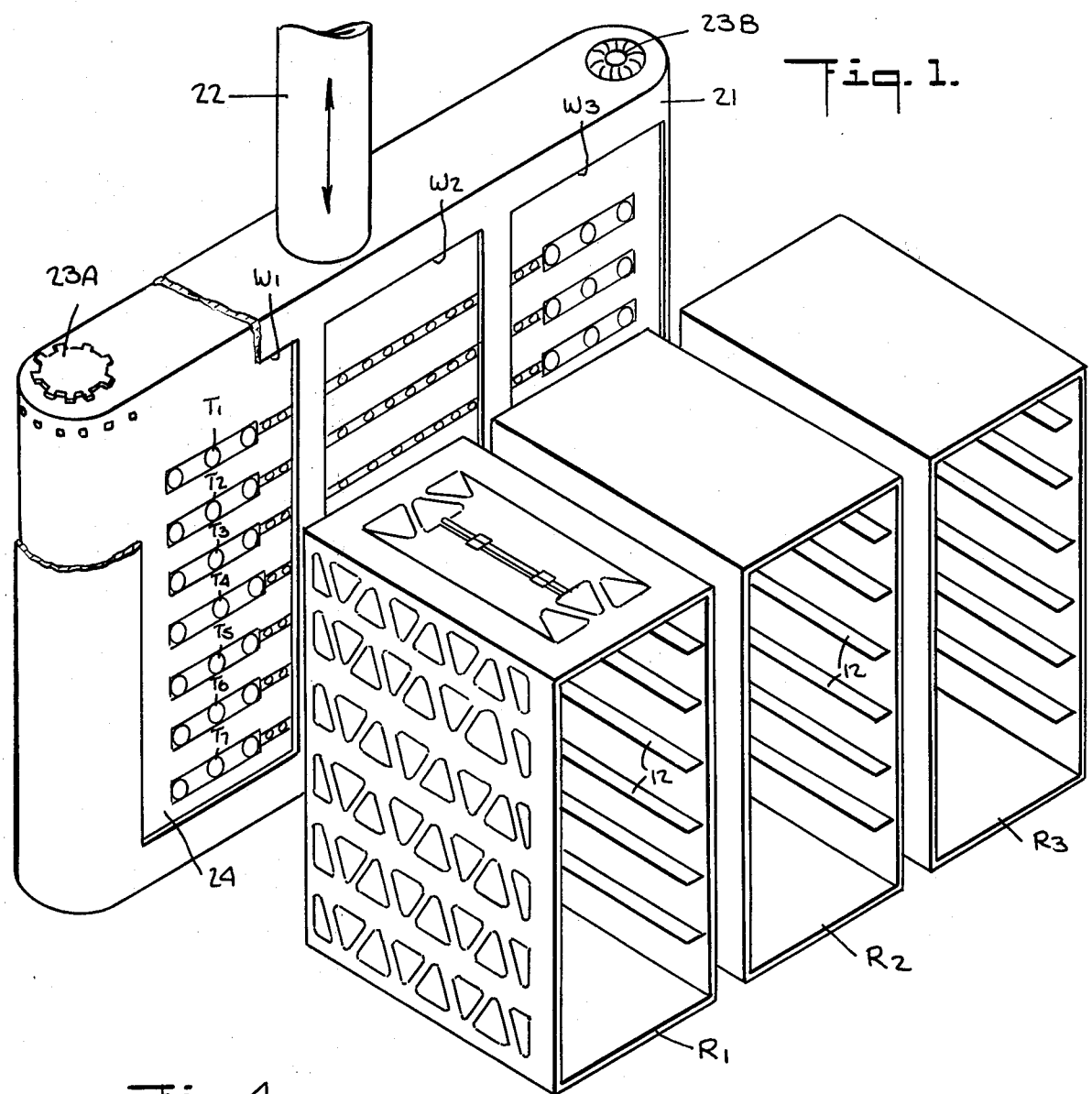
Figure 2:
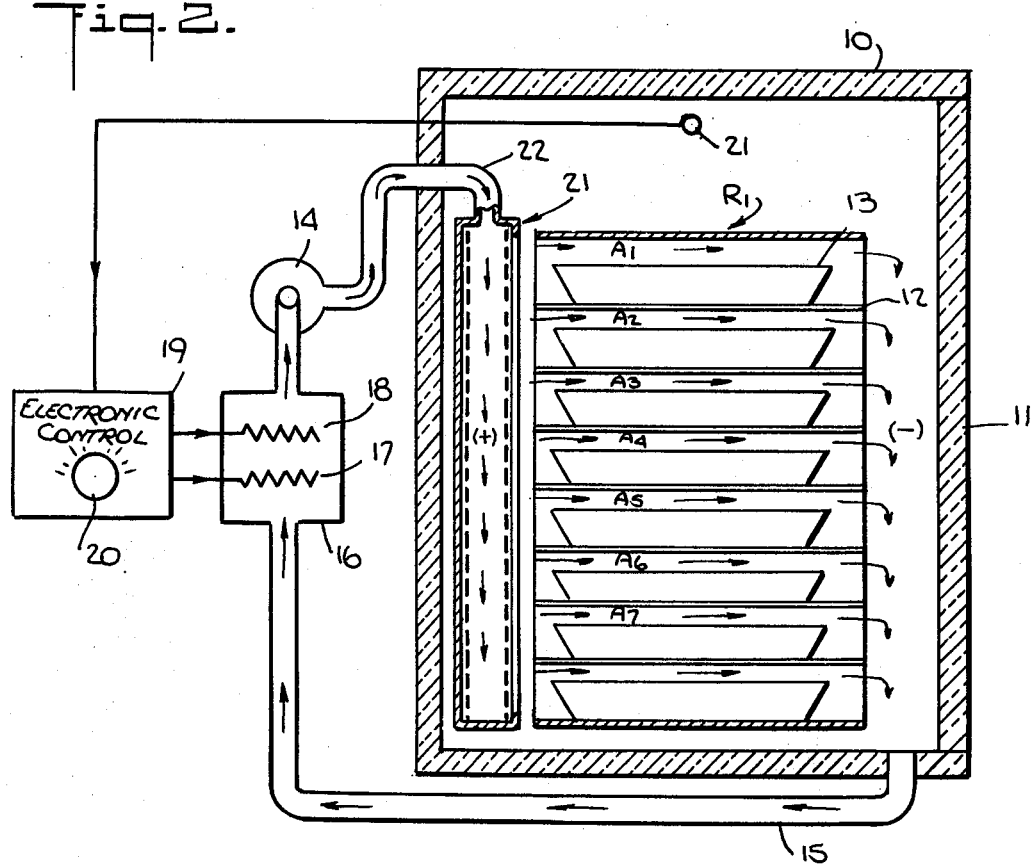
Figure 3:
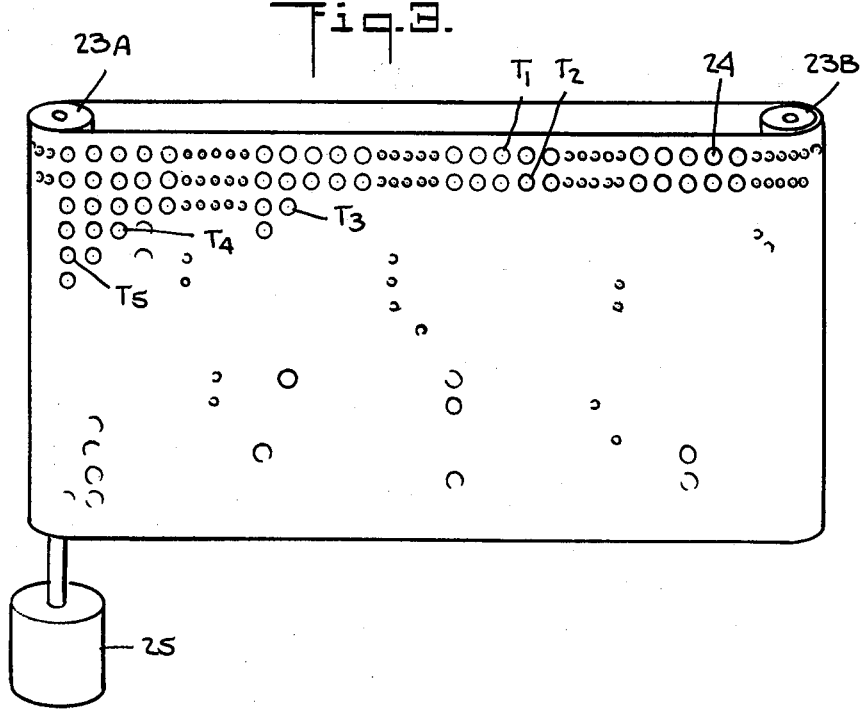

Referring now to FIGS. 1 and 2, there is shown a system in accordance with the invention for rapidly raising the temperature of a pre-cooked meal or other product having low thermal conductivity from a cold or frozen state to a heated state in a manner bringing the internal temperature of the entire body of the product to substantially the same predetermined temperature level, the internal temperature of the product thereafter being maintained at the desired level for an indefinite period, the internal temperature being uniform throughout the food body.

Thermal conductivity is defined by the quantity of heat which flows in unit time through a unit area of a plate of unit thickness having unit differences of temperature between its faces. There is no generally accepted combination of units for expressing thermal conductivity. One common combination of units for stating thermal conductivity is in British units where $k = BTU/(ft^2)(h)$ for 1-inch thick plate/F.°.

In British thermal units, the thermal conductivity of silver at room temperature is 2824, which is very high; whereas that of ice is 15, this representing a quite low value of thermal conductivity. Frozen or refrigerated food has a low value thermal conductivity close to that of ice. Since the rate at which heat is conducted through a body is a function of its thermal conductivity, it is evident that heat is conducted at a much faster rate through silver than through frozen food. The manner in which a system in accordance with the present invention accommodates itself to the low conductivity of the product being heated to effect rapid heat of the product without overheating thereof will be later explained.

And since a system in accordance with the invention makes use of heated air, the distinction between natural and forced convection must be understood. Natural convection is a transfer of heat to and from a surface by the movement of a fluid when this movement is caused solely by a difference in fluid density. But in forced convection, the velocity of the fluid is dominant factor for heat transfer. The present invention makes use of forced convection with respect to the sides of the food-loaded tray being heated to effect heat transfer at a very rapid rate.

A system in accordance with the invention includes a thermally-insulated bunker or locker 10 suitable for installation in an aircraft, the locker having a front door 11 to provide access to the interior thereof. The dimensions of the locker are such as to accommodate a bank of three open-ended racks, $R_1$, $R_2$ and $R_3$, which in practice may be of aluminum construction or of disposable cardboard or plastic material.

Each rack includes ledges 12 on either side thereof, serving as tracks to receive a stack or trays 13 loaded with pre-cooked meals in the cold state. The positions of the ledges and the height of the trays are such as to create horizontal air spaces $A_1$, $A_2$, etc. between the trays in the stack. In practice, instead of a single tray on each level in the rack, the dimensions of the rack may be such as to accommodate two or more trays per level. In practice, the trays may be loaded in the racks at the commissary and transported to the airport.

Air is drawn from the locker in the free region between the front ends of racks $R_1$, $R_2$ and $R_3$ and door 11, this action being effected by an external blower 14 which is coupled to the region by a duct 15. A heater station 16 is interposed between blower 14 and duct 15, this station having a high wattage electrical heater element 17 and a low wattage element 18. Operation of the heater elements is effected by an electrical control circuit 19 provided with a timer 20, the circuit being responsive to a signal obtained from a temperature sensor 21 installed in the locker. Air drawn through heater station 16 is forced by blower 14 into an air modulator 21 through an upper inlet 22. The modulator is placed in the locker between the rear ends of racks $R_1$, $R_2$ and $R_3$ and the rear wall of the locker.

As shown in FIG. 1, air modulator 21 has a shallow cartridge or box-like formation, the front wall of the box having windows $W_1$, $W_2$ and $W_3$ therein. These windows register with the rear ends of racks $R_1$, $R_2$ and $R_3$ so that air emerging from each window is confined to a respective rack.

Mounted within box 21 between end rollers 23A and 23B is a broad continuous tape 24, the tape being advanced by a motor 25 operatively coupled to roller 23A which acts as the drive roller. Tape 24, which may be fabricated of synthetic plastic flexible film material capable of withstanding the temperatures involved, has punched therein several endless trains of spaced holes which extend in parallel longitudinal paths. Each of these trains $T_1$ to $T_7$ lies in a horizontal plane that intersects a respective air space ($A_1$ to $A_7$) in the bank of racks, so that hot air is projected by the holes in the trains into the air spaces.

Figure 4:
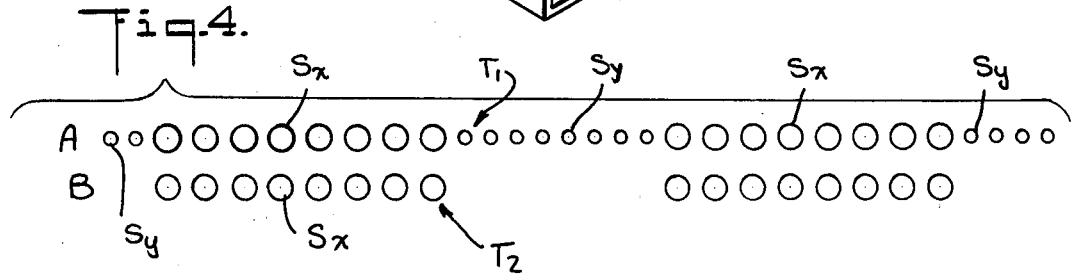
FIG. 4 illustrates one of the trains of holes on the tape.
Figure 5:
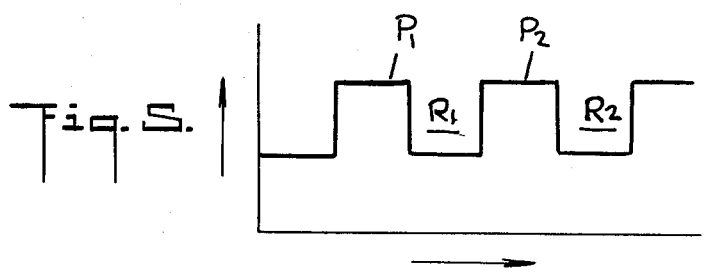
FIG. 5 is a graph showing the pulsatory hot air pattern.

As shown separately in FIG. 4, each train, such as train $T_1$, is composed of alternating large-hole and small-hole sections $S_x$ and $S_y$. Consequently, when section $S_x$ is in alignment with window $W_1$, a large volume of hot air is projected therethrough into rack $R_1$; and when a section $S_y$ is in alignment therewith, a much smaller volume of air is projected. The train pattern shown in FIG. 4 is by way of example only and the pattern may, for example, be composed of alternate hole and no-hole sections. The resultant pulsatory hot air wave, as shown in FIG. 5, is composed of periodic hot air pulses $P_1$, $P_2$, etc., separated by relaxation intervals $R_1$, $R_2$, etc.

When the train is composed of large hole and small hole sections, pulses $P_1$ etc. are each formed by a large volume of air at an elevated temperature, and the relaxation intervals by a small volume of air at the same temperature. But when the relaxation intervals are intervals of no-flow, then heat-transfer in these intervals is well below that of the pulses. In either case, the effect is the same; for a small volume of air produces relatively little heat transfer and is equivalent to a reduced temperature interval.

In practice, motor 25 for driving the tape may have a stepping action such as to advance the front course of the alternate train sections of the tape into registration with the windows $W_1$, $W_2$ and $W_3$, at which point movement is halted for, say, one minute, after which there is another advance to bring the next section into registration. Thus window $W_1$ periodically sees a large-hole section for one minute, followed by a small-hole section to effectively produce square wave pulses. But if the tape is advanced continuously, the pulsatory wave is sinusoidal in form.

In the arrangement shown in FIG. 2, because air is drawn from the free region of the locker, the pressure in this region is negative with respect to the positive pressure (+) produced in the air modulator 21 into which the hot air is forced. Because of the resultant pressure differential between the open front ends of the racks and the open rear ends thereof, air is caused to flow through air space $A_1$ to $A_7$ at high velocity, this producing forced convection which markedly increases the rate of heat transfer. The entire locker, save for the air modulator, is under negative pressure.

The pulsatory wave heat-up phase, which may last a half hour or longer, depending on the product load and its initial low temperature, promotes rapid-heat transfer without, however, raising the surface temperature of the body of the product above the predetermined elevated level. Thus in the heat-up phase, the temperature of the product is never in the case of pre-cooked food raised to a level that would cause the the food to be recooked.

The heat-up phase in a system in accordance with the invention is of relatively short duration and may be in a range of $\frac{1}{2}$ hour to an hour, depending, of course, on the magnitude of the food load placed in the unit and the initial cold temperature of this load. The reason the heat-up phase is brief is that the rate of heat transfer is fast throughout this phase, not merely at the outset of this phase.

The fluidic pulses have a temperature well above the service temperature level to which the food is to be raised from the cold state. The relaxation intervals between pulses are effectively at a lower heat-transfer because of the reduced volume of air or the absence of flow, depending on the train hole pattern on the tape.

Because the hot air temperature of the pulsed air in the heat-up phase is significantly higher (i.e., 190° F.) than the food service temperature level (i.e., 150° to 160°), even though the temperature differential between the hot air temperature and the prevailing food temperature is greatest at the outset of the heat-up phase, it never reaches a condition where this differential is small. Even as the food temperature approaches the service temperature, say, at 135° F., the differential between the then prevailing temperature and the hot air temperature remains fairly large and the rate of heat transfer is therefore still quite rapid.

Hence, instead of having a food temperature vs. time curve for the heat-up phase—which is steep for the first 10 minutes or so of heat-up and then proceeds to level off to a degree that it takes an extended time to raise the temperature of the food to the service level—with the pulsed air technique in accordance with the invention, though the curve becomes somewhat less steep as one approaches the service level, at no time does the curve reflect a low heat-up rate.

In contradistinction, in a continuously-heated conventional oven, if the oven temperature is maintained at a substantially very high level to effect rapid heat-up of the pre-cooked food, the temperature will then be such as to cause undesirable recooking of the food. And if the oven temperature is maintained at a much lower constant level to heat up the food without recooking thereof, then the heat-up period becomes unduly prolonged. With the present system, which makes use of a pulsatory heat wave in a forced convection arrangement, the rate is rapid for the entire range of food temperatures, running from an initial cold temperature to a hot service temperature at the completion of the heat-up phase without danger of re-cooking the food despite the high peak temperature of the pulses.

The rate of pulsing is a critical aspect of the present invention; for a body of cold or frozen food may be regarded as formed of a succession of layers going from the outer surface to the core. The core can only be heated by transmitting heat through successive layers of poor thermal conductivity from the exterior to the interior.

Assuming, therefore, that the outer layer is initially at 10° F. and is subjected for about one minute to a hot air pulse ($P_1$, $P_2$, etc.) having a temperature of 190° F. (one half cycle) and the velocity of hot air flowing past the body of the food is such as to raise the temperature of the outer layer to, say, 20° F., then in the next half cycle (represented by relaxation intervals $R_1$, $R_2$, etc.) which also lasts about a minute and in which the air is quiescent, heat from the 20° F. outer layer is transferred to a second underlying layer which is thereby raised in temperature from 10° F. to 15° F., with a resultant reduction in temperature of the outer layer to, say, 15° F. Thus the interval between hot air pulses represents a dwell or relaxation period during which interval heat transfer takes place in the cold food body.

When the outer layer, now at 15° F., is subjected to the next hot air pulse at 190° for a minute, this will raise the temperature of the outer layer to, say, 25° F.; and during the next minute interval when the air is again quiescent, there will be a heat transfer from the outer layer to the second layer, this time raising the temperature of the second layer to 20° F. and reducing the outer layer to 20° F. It is to be understood that these temperature values are but one example of a usable pulsatory heat wave.

Similar heat transfer actions take place concurrently between the second and third layers and between the third and fourth layers and so on, very much in the fashion of an electronic cascade counter. In a counter, when an input signal (a heat pulse) is received, the state of each stage (i.e., layer) in the cascade is advanced in an ordered sequence. Thus the intervals between hot air pulses applied to the outer layer of the cold body allow time for transfer of heat to be effected from layer to layer. Because the outermost layers which are subjected to a temperature well above the service temperature are permitted to cool down in these intervals, the temperature of these layers is never permitted to rise above the service temperature and excessive heating is avoided.

The duration of the heat-up phase is controlled by timer 20 which is preset to a time period appropriate to the food load. At the conclusion of heat-up phase, the electronic control reduces the temperature of the air blown into the air modulator to the desired service temperature level. To this end, during the heat-up phase, both the high wattage electrical heater elements 17 and the low wattage element 18 are energized; whereas during the service phase, only the low wattage element is energized, this element being thermostatically regulated through sensor 21 to maintain the desired service temperature level.

Other Applications, Modifications and Features

While the invention has been described herein as applied to aircraft lockers, it is to be understood that the system is also usable in railroad train and ship galleys or wherever space for heating food is at a premium. A significant advantage of the invention and one reason it lends itself to installation in tight spaces is that the system uses a relatively small volume of air as compared to systems of the type disclosed in my prior patent applications and patents; for while the air modulator is supplied with a continuous flow of heated air, this flow is selectively and sequentially directed into the racks within the locker, no heated air being wasted. In practice, the heat source may be a remote, self-contained, compact unit with a blower, heater and controls, this unit being easily installed.

Another significant aspect of the invention is that the temperature of the air to effect food heating may be much lower than in a conventional aircraft oven; where in order to rapidly heat the meals, the oven temperature is usually well above 200° F. This oven temperature sometimes results in burned meals. In the present system, since the heated air is blown through the tray-filled racks containing the meals at high velocity, the air temperature may be relatively low. The rate of heat transfer is a function of air velocity as well as temperature; hence by using a high velocity stream, one can effect rapid heat transfer at a fairly low temperature as compared to conventional ovens.

Also, while the racks $R_1$, $R_2$ and $R_3$ are shown as having ledges therein to maintain the trays with air spaces therebetween, in practice, particularly when use is made of cardboard racks, instead of ledges, the food trays may include spacer elements, so that when stacked in the racks, air spaces are formed between the trays to admit the heated air.

It is also important to realize that the racks need not be a permanent part of the system, but can represent portable elements used to transport the food trays to the locker. In some cases, these racks may be disposable.

In the system shown, the air modulator is placed in the rear of the locker behind the bank of racks. In practice, the modulator may be provided with rear as well as front windows, with the modulator being placed in the locker so as to cooperate with a rear bank as well as a front bank of racks, in which case the modulator would be about centered in the locker. The invention is therefore not limited to any specific modulator placement.

Alternative Embodiment

Figure 6:
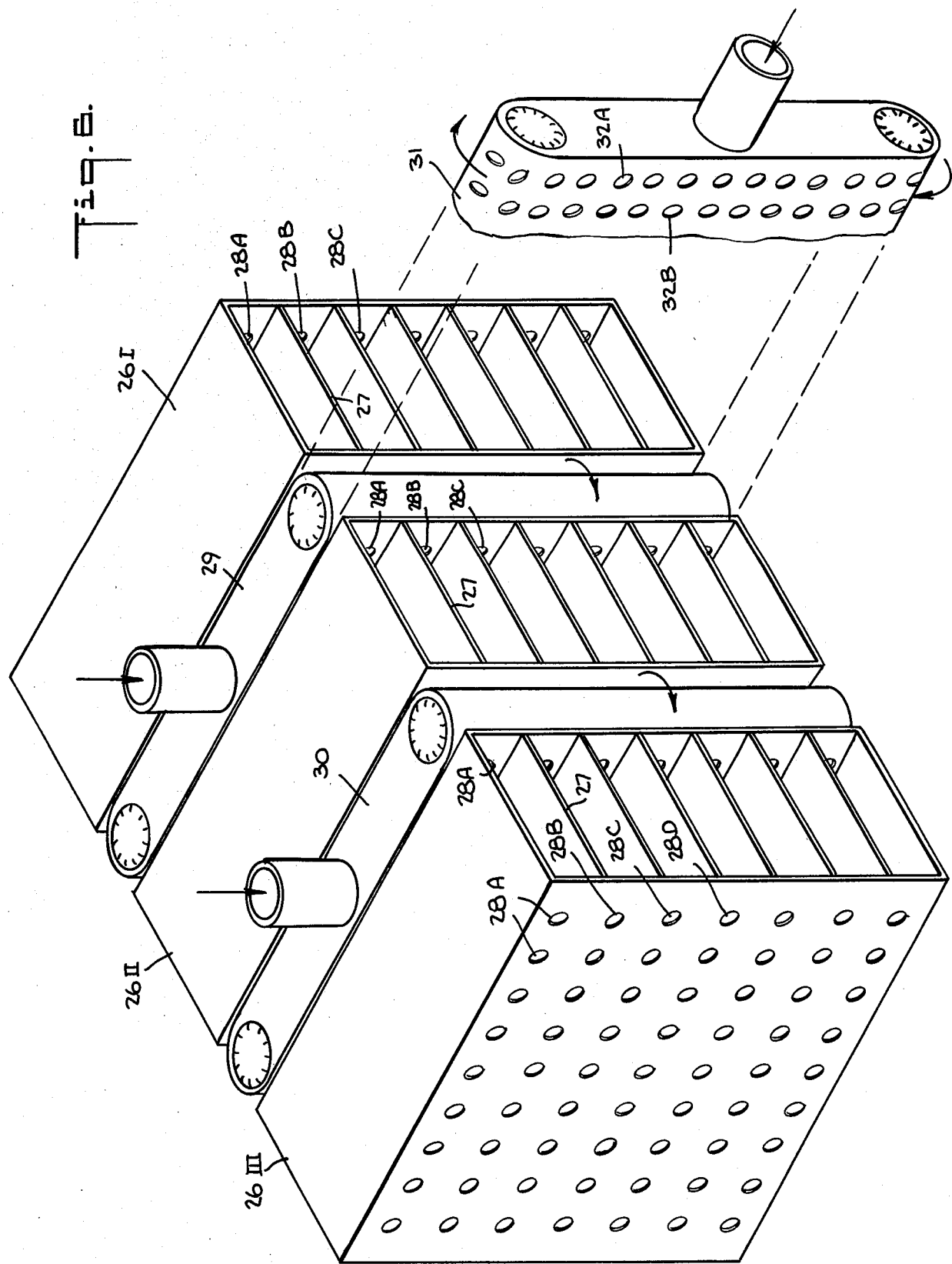
FIG. 6 shows an alternative embodiment.

In the embodiment of the system shown in FIG. 6, the three racks 26I, 26II and 26III which are placed within a locker or galley have shelves 27 to define compartments for accommodating the trays. The opposing side walls of the racks are ventilated by holes, there being a longitudinal row of holes for each compartment. Thus the top compartment has a row of holes 28A, the one below 28B, the third 28C, etc.

In this arrangement, an air modulator 29 is sandwiched between the adjacent ventilated side walls of racks 26I and 26II, and a like air modulator 30 between the adjacent side walls of racks 26II and 26III. The modulators each have a continuous tape 31 provided with parallel rows of holes 32A, 32B, etc., which cooperate with the rows of holes in the side walls so that as the tape advances, the tape holes in each row go in and out of registration with the holes in the rack sides. As a consequence, the hot air under pressure in each modulator box is periodically admitted into the associated compartments, air flow being cut off when the tape holes are out of registration with the rack wall holes, thereby providing a pulsatory air flow pattern.

In all other respects, the operation of this arrangement is essentially the same as in the first embodiment.

While there has been shown and described a preferred embodiment of galley meal processing system in accordance with the invention, it will be appreciated that many changes and modifications may be made therein without, however, departing from the essential spirit thereof.

I claim:

1. A system usable in aircraft for serving passengers with trays loaded with pre-cooked means that are raised in temperature from an initially cold state to a service temperature level and held at that level until it is time to serve, said system comprising:
   A. a locker having a front access door;
   B. a bank of open-ended racks receivable in said locker, the front ends of the racks facing the door to define a free region therebetween, each rack accommodating a stack of said trays with spaces therebetween, the correspondingly-positioned spaces in the racks lying in parallel tiers;
   C. an air modulator interposed between the rear ends of the racks and the rear of the locker, said modulator being in the form of a shallow box having supported therein a continuously-driven tape whose front course faces the rear end of the racks, said tape having formed therein parallel endless trains of holes, each train lying in a plane intersecting a respective tier, the front of the box having windows therein which expose the rear ends of the racks to said train, and a heating station means to draw air from the free region and to heat this air before blowing it into the box whereby heated air is projected through the holes in the trains and projected into said air spaces to heat the loaded trays.

2. A system as set forth in claim 1, wherein said locker is thermally insulated.

3. A system as set forth in claim 1, wherein each train is composed of alternate large-hole and small-hole sections, whereby the hot air projected into each rack assumes a pulsating waveform.

4. A system as set forth in claim 1, wherein each train is composed of alternate sections one of which has holes therein, the other of which has no holes therein, whereby the hot air projected into each rack assumes a pulsatory waveform.

5. A system as set forth in claim 1, wherein said means to draw air from the free region includes a duct which passes the air through a heater station into a blower which forces the heated air into the air modulator.

6. A system as set forth in claim 5, wherein said heater station has high and low wattage heater elements which are both energized in a heat-up phase when the meals are raised to a service temperature level, only the low wattage heater being energized during the subsequent service phase.

7. A system as set forth in claim 1, wherein said tape is made of synthetic plastic film material.

8. A system as set forth in claim 7, wherein said tape is driven to advance continuously.

9. A system as set forth in claim 7, wherein said tape is driven to advance in a stepwise manner.

10. A system for serving diners with trays loaded with pre-cooked meals that are raised in temperature from an initially cold state to a service temperature level, said system comprising:
    A. a locker;
    B. a bank of open-ended racks receivable in said locker, each rack accommodating a stack of said trays with air spaces therebetween;
    C. an air heating station; and
    D. an air modulator disposed in said locker in the form of a shallow box having supported therein a continuously-driven tape having a moving course facing the rear end of the racks in the bank, said tape having a pattern of holes therein, and means to draw air from the locker and to heat the air in said heating station before blowing it into the box, whereby heated air is emitted through the holes of the modulator and projected into said air spaces to heat the loaded trays.

11. A system for serving diners with trays or other food packages loaded with pre-cooked meals that are raised in temperature from an initially cold state to a service temperature level, said system comprising:
    A. at least one rack for accommodating a plurality of said packages one above the other with the air spaces therebetween;
    B. an air heating station; and
    C. an air modulator cooperating with said rack and provided with a continuously driven tape having a pattern of holes therein, heated air drawn from said station being forced into the region within the tape whereby the air is ejected from the holes into said rack and passes through said air spaces to heat the food in said packages.

12. A system as set forth in claim 11, wherein said rack is divided into compartments and includes a wall having holes ventilating the compartments, and said tape has holes which fall in and out of registration with the wall holes as the tape advances.

* * * * *